United States Patent [19]

Robertson

[11] Patent Number: 4,631,279

[45] Date of Patent: Dec. 23, 1986

[54] 6-(PYRIDINYLPHENYL)DIHY-DROPYRIDAZINONES AS INOTROPIC AGENTS

[75] Inventor: David W. Robertson, Indianapolis, Ind.

[73] Assignee: Eli Lilly and Company, Indianapolis, Ind.

[21] Appl. No.: 660,840

[22] Filed: Oct. 15, 1984

[51] Int. Cl.$^4$ .................. C07D 401/10; C07D 213/55; C07D 211/20; A61K 31/50

[52] U.S. Cl. .................................. 514/247; 544/238; 546/226; 546/238; 546/339; 546/342

[58] Field of Search .......................... 544/238; 514/247

[56] References Cited

U.S. PATENT DOCUMENTS

| | | | |
|---|---|---|---|
| 3,845,050 | 10/1974 | Lebkuecher et al. | 544/238 |
| 3,975,388 | 8/1976 | Hakim et al. | 544/238 |
| 4,177,273 | 12/1979 | Bennett | 424/250 |
| 4,289,774 | 9/1981 | Schacht | 544/238 |
| 4,298,609 | 11/1981 | Lesher | 544/238 |
| 4,304,777 | 12/1981 | Lesher et al. | 424/250 |
| 4,353,905 | 10/1982 | Sircar et al. | 424/250 |
| 4,397,854 | 8/1983 | Sircar | 424/250 |
| 4,404,203 | 9/1983 | Sircar | 424/250 |
| 4,508,721 | 4/1985 | Hargreaves | 544/238 |
| 4,521,416 | 6/1985 | Sircar et al. | 544/238 |
| 4,551,455 | 11/1985 | Hilboll et al. | 514/252 |

OTHER PUBLICATIONS

Sloboda, Chem. Abs., 87, 78232t (1977).
Kalkarni, Chem. Abs., 88, 98934x (1977).
Kaddah, Chem. Abs., 88, 152531d (1977).
Child, J. Pharm. Sci., 66, 466 (1977).
Nakao et al, Chemical Abstracts, 91:39511w (1979).
M.T.C. Inc., Chemical Abstracts, 101:90957y (1984).
Curran et al., J. Med. Chem., 17(3), 273 (1974).
McEvoy et al., J. Med. Chem., 17(3), 281 (1974).
Derwent, 18918K/08 abstracting Japanese Patent J58008016.

*Primary Examiner*—Mark L. Berch
*Attorney, Agent, or Firm*—Robert A. Conrad

[57] ABSTRACT

This invention provides certain pyridazinone derivatives, their pharmaceutical formulations, and their use as positive inotropic agents.

20 Claims, No Drawings

6-(PYRIDINYLPHENYL)DIHYDROPYRIDAZINONES AS INOTROPIC AGENTS

BACKGROUND OF THE INVENTION

The cardiac glycosides and the sympathomimetic amines are the principal inotropic agents used in the management of congestive heart failure. Although the cardiac glycosides, especially digitalis, are among the most frequently prescribed drugs, they have numerous liabilities such as a low therapeutic index and erratic absorption, and are associated with life-threatening arrhythmias and deleterious drug-drug interactions. In addition, many patients either do not respond, or become refractory to these agents. The sympathomimetic amines, such as dopamine and epinephrine, have limited utility due to positive chronotropic effects, arrhythmogenic properties, and oral ineffectiveness.

More recently, new classes of inotropic agents have been found. These include certain dihydropyridazinone derivatives such as those taught in U.S. Pat. Nos. 4,353,905, 4,361,563, 4,304,777, and 4,404,203 which cause an increase in myocardial contractility in anesthetized dogs and cats. Other pyridazinone derivatives are taught in the art to be cardiotonics, anti-hypertensives, and antithrombotic agents; see, e.g., U.S. Pat. No. 4,258,185.

The present invention provides certain pyridazinone derivatives which are potent, long-acting, orally effective positive inotropic agents which cause minimal effects on blood pressure and heart rate.

SUMMARY OF THE INVENTION

This invention provides compounds of the formula I

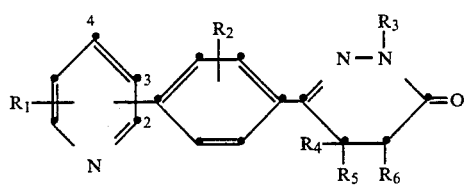

wherein $R_1$, $R_2$, $R_3$, $R_4$, $R_5$, and $R_6$ are independently hydrogen or $C_1$–$C_4$ alkyl, or $R_6$ and one of $R_4$ and $R_5$ taken together form a bond; and pharmaceutically acceptable acid addition salts thereof.

This invention also provides a method of treating a mammal, including a human subject, suffering from or susceptible to heart failure, which comprises administering to said mammal an effective amount of a compound of the above formula.

According to a further aspect of the present invention, there are provided pharmaceutical formulations which comprise as active ingredient a compound of Formula I in association with a pharmaceutically acceptable carrier, diluent, or excipient therefor.

DETAILED DESCRIPTION AND PREFERRED EMBODIMENTS

The term "$C_1$–$C_4$ alkyl" when used herein refers to the straight and branched aliphatic radicals of one to four carbon atoms, and includes methyl, ethyl, propyl, isopropyl, butyl, isobutyl, sec-butyl, and tert-butyl.

A preferred group of compounds are those of the above formula wherein (a) each of $R_1$, $R_2$, $R_3$, and $R_6$ is hydrogen;
(b) one of $R_4$ and $R_5$ is hydrogen;
(c) the other of $R_4$ and $R_5$ is hydrogen or methyl; and
(d) the pyridine ring is attached at its 3-position to the phenyl substituent.

An especially preferred compound is 4,5-dihydro-6-[4-(3-pyridinyl)phenyl]-3(2H)-pyridazinone or a pharmaceutically acceptable salt thereof.

The compounds of the present invention can be prepared by any of several methods known to those skilled in the art. In addition to their utility as inotropic agents, the compounds of the present invention wherein $R_3$ is hydrogen are also useful as intermediates to the compounds of the invention wherein $R_3$ is $C_1$–$C_4$ alkyl. This intraconversion may be performed by an appropriate alkylation reaction according to procedures well known to those skilled in the art.

A typical synthesis of the compounds of this invention is depicted in Scheme I.

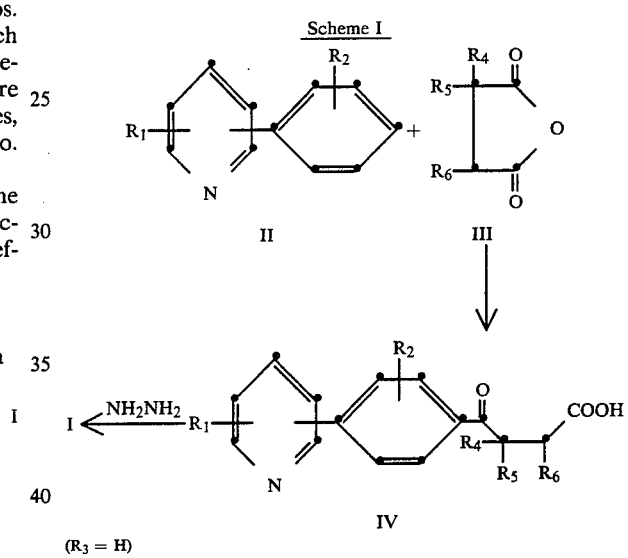

As summarized by Scheme I above, a preferred method of making the compounds of Formula I wherein $R_3$ is hydrogen comprises reacting the appropriately substituted phenylpyridine II with a maleic or succinic anhydride derivative III, in the presence of a Lewis acid such as aluminum chloride, and in the presence of a nonreactive solvent, for example a halogenated alkane such as tetrachloroethane, a dialkylformamide such as dimethylformamide, or the like. This reaction is a standard Friedel-Crafts acylation reaction and is generally complete within about 24 hours when carried out at a temperature from about 25° C. up to the reflux temperature of the reaction mixture, for example about 150° C. This reaction provides the corresponding gamma-keto-acid IV, which can be reacted with hydrazine or hydrazine hydrate in the absence of a solvent, or if preferred in the presence of an inert solvent such as water, an alcohol such as ethanol, tetrahydrofuran, toluene, dimethylformamide, or the like, at a temperature ranging from about 20° C. to the reflux temperature of the reaction mixture. The compounds thus formed are compounds of Formula I wherein $R_3$ is hydrogen, which may be further transformed to other compounds of Formula I by alkylation as previously described.

When intermediate III is unsymmetrical, two possible products from the acylation are possible. In such cases, acylation of II with intermediate V

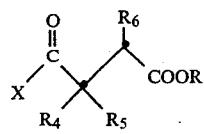

where X is bromo or chloro and R is, for example, $C_1$–$C_4$ alkyl, preferably methyl or ethyl, under standard acylation conditions, gives the ester derivative of intermediate IV which can be transformed into I ($R_3$=H) in the same way as previously described.

The above scheme provides the best yields for the preparation of the preferred 3-pyridyl isomer. An alternate procedure for preparing the 2- and 4- isomers is summarized in Scheme II. The scheme is drawn for the 2-pyridyl isomer, but the same sequence can be used to prepare the corresponding 3- and 4-isomers.

example, by basic hydrolysis, to provide intermediate XI which can then be dehydrogenated by standard techniques to intermediate XII. The preferred dehydrogenation reaction consists of heating intermediate XI to 250° C. in biphenyl in the presence of palladium on carbon. Intermediate XII can then be transformed into I ($R_3$=H) by the methods as previously described in Scheme I.

Alternatively, VIII may be acylated with the appropriate acid chloride or anhydride to form XIII.

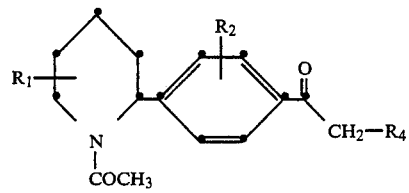

XIII may be transformed by the deprotection and dehydrogenation conditions described above to produce XIV.

Scheme II

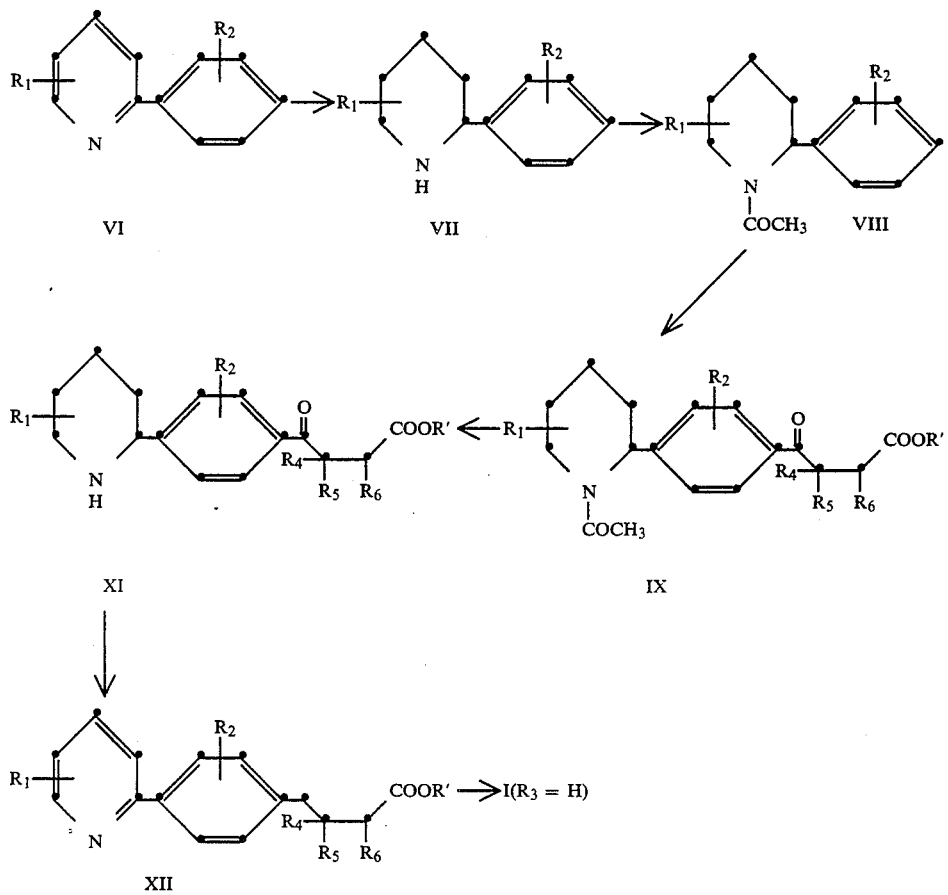

where R' is hydrogen or, for example, $C_1$–$C_4$ alkyl.

A phenylpyridine VI can be transformed to the corresponding piperidine VII according to standard methods of reduction, such as hydrogenation. The piperidine can be protected by acylation, for example through acetylation, according to standard acylating techniques, and the resulting intermediate VIII can then be acylated with intermediate III or V in the same way as described above to provide the gamma-keto acid or ester, intermediate IX. The protecting group can be removed, for

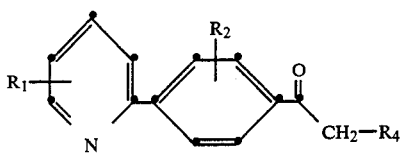

(XIV)

This intermediate may then be converted to XII by methods taught in U.S. Pat. No. 4,258,185, i.e., a Mannich reaction followed by quaternization, reaction with cyanide, and hydrolysis.

Intermediates II, III, V, and VI as well as the other necessary reagents are commercially available, are known in the literature, or can be prepared by methods known in the art.

Depending upon the definitions of $R_4$, $R_5$, and $R_6$, the compounds of Formula I may exist as stereoisomers. This invention is not limited to any particular isomer but includes all possible individual isomers, racemates, and diastereomers of the compounds of Formula I.

The pharmaceutically acceptable acid addition salts of this invention include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxy-alkanoic and -alkanedioic acids, aromatic acids, aliphatic and aromatic sulfonic acids, and the like. Typical pharmaceutically acceptable salts of the invention thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, $\beta$-hydroxybutyrate, glycolate, malate, tartrate, methanesulfonate, propanesulfonate, naphthalene-1-sulfonate, naphthalene-2-sulfonate and the like salts. The preferred salts of this invention are those derived from inorganic acids, especially hydrochloric acid.

The following example further illustrates the preparation of the compounds of this invention. The example is illustrative only and is not intended to limit the scope of the invention in any way.

EXAMPLE 1

4,5-Dihydro-6-[4-(3-pyridinyl)phenyl]-3(2H)-pyridazinone

A. Preparation of 3-[4-(4-ketobutanoic acid)phenyl]pyridine.

Aluminum chloride (13.8 g) was added in portions to a solution of 5.0 g of 3-phenylpyridine and 3.55 g of succinic anhydride in 100 ml of 1,1,2,2-tetrachloroethane. The solution was heated to 60° C. for approximately 18 hours and then poured into a mixture of ice and concentrated hydrochloric acid. The mixture was adjusted to a pH of 5-6 with 50% sodium hydroxide. The resulting precipitate was filtered and discarded. The filtrate was extracted with ethyl acetate. The organic extracts were combined, washed with a saturated sodium chloride solution, dried over sodium sulfate, and concentrated in vacuo. The resulting solid was chromatographed over silica gel. The appropriate fractions were combined and evaporated to dryness. The residue was crystallized from dimethylformamide/water to provide 1.9 g of the desired subtitle intermediate, m.p. 225°-228° C.

Analysis for $C_{15}H_{13}NO_3$; Calculated: C, 70.58; H, 5.13; N, 5.49; Found: C, 70.30; H, 5.15; N, 5.35.

B. Preparation of 4,5-dihydro-6-[4-(3-pyridinyl)phenyl]-3(2H)-pyridazinone

A mixture of 1.69 g of 3-[4-(4-ketobutanoic acid)-phenyl]pyridine and 0.86 ml of 85% hydrazine hydrate in 250 ml of absolute ethanol was heated to reflux for 12 hours. The mixture was cooled to 0° C. and filtered. The recovered solid was crystallized from dimethylformamide/water to provide 1.1 g of the desired title product as a yellow solid, m.p. 225°-226° C. The proton NMR and mass spectral data were consistent with the assigned structure. Analytical HPLC indicated the product had a purity in excess of 99.5%.

Analysis for $C_{15}H_{13}N_3O$; Calculated: C, 71.70; H, 5.21; N, 16.72; Found: C, 71.03; H, 5.41; N, 15.44.

The following compounds can be prepared according to the synthesis described in Example 1, Scheme II, or by other methods generally known in the art.

4,5-dihydro-6-[4-(2-pyridinyl)phenyl]-5,5-dimethyl-3(2H)-pyridazinone,
6-[4-(3-methyl-4-pyridinyl)phenyl]-5-methyl-2-ethyl-3(2H)-pyridazinone,
4,5-dihydro-6-[3-propyl-4-(3-pyridinyl)phenyl]-4,5-dimethyl-3(2H)-pyridazinone,
6-[4-(2-propyl-4-pyridinyl)phenyl]-4,5-diethyl-2-butyl-3(2H)-pyridazinone,
4,5-dihydro-6-[4-(3-pyridinyl)phenyl]-4-methyl-3(2H)-pyridazinone,
4,5-dihydro-6-[2-ethyl-4-(4-pyridinyl)phenyl]-5-sec-butyl-3(2H)-pyridazinone,
4,5-dihydro-6-[2-isopropyl-4-(4-t-butyl-2-pyridinyl)-phenyl]-2-isopropyl-4-ethyl-3(2H)-pyridazinone,
6-[3-methyl-4-(4-pyridinyl)phenyl]-4,5-dimethyl-3(2H)-pyridazinone,
4,5-dihydro-6-[4-(4-pyridinyl)phenyl]-4-methyl-3(2H)-pyridazinone,
4,5-dihydro-6-[4-(2-pyridinyl)phenyl]-3(2H)-pyridazinone,
6-[2-propyl-4-(3-pyridinyl)phenyl]-4-methyl-2-t-butyl-3(2H)-pyridazinone,
6-[4-(3-pyridinyl)phenyl]-3(2H)-pyridazinone,
6-[4-(3-pyridinyl)phenyl]-4-methyl-3(2H)-pyridazinone,
4,5-dihydro-6-[4-(4-pyridinyl)phenyl]-2,4,5,5-tetramethyl-3(2H)-pyridazinone,
4,5-dihydro-6-[4-(3-pyridinyl)phenyl]-2,4-dimethyl-3(2H)-pyridazinone.

The compounds of Formula I are particularly useful as inotropic agents due to their potency, long action of effect, and oral efficacy; they are therefore useful in the treatment and prevention of heart failure. For example, the compound of Example 1 was examined as to its pharmacodynamic effects in the following test systems.

Positive Inotropic Activity in Isolated Cat Papillary Muscles

Cats of either sex were anesthetized with Metofane (1,1-difluoro-2,2-dichloroethyl methyl ether, Pittman-Moore). Their hearts were immediately removed and the papillary muscles dissected and suspended in individual organ baths. A platinum hook secured one end of the muscle to an electrode mounted in the bottom of the bath, and a silk thread attached the tendon to a Statham isometric transducer. The baths contained Krebs-Henseleit solution (36° C., bubbled with 95 percent oxygen—5 percent carbon dioxide) of the following millimolar composition: NaCl, 118; KCl, 4.5; $CaCl_2$, 2.5; $KH_2PO_4$, 1.1; $MgSO_4$, 1.2; $NaHCO_3$, 25; and glucose, 11.

A base-line tension of 1.5 g was applied to each muscle. Square-wave pulses (5.0 msec. in duration, three times threshold voltage) delivered through the hook electrode and a second electrode positioned near the top of the muscle evoked 12 contractions/minute, which were recorded on a Grass polygraph. After the muscles had equilibrated for 60 minutes, the recorder gain was adjusted so that the pen deflected 10 mm. The test compound was introduced in a solution of normal saline in an amount to bring the final concentration of the compound to $10^{-5}$ or $10^{-4}$ molar. Increases in contractility were tabulated as millimeters of pen deflection in excess of the baseline value. In each experiment the maximum contractility was measured. Test results are summarized as percent of control (control = 100 percent). Values are the average of results from 2 to 8 muscles. The compound of Example 1 caused peak increases of 173% and 257% at concentrations of $10^{-5}M$ and $10^{-4}M$, respectively.

Experiments in Anesthetized Dogs

Mongrel dogs of either sex ranging in weight from 7 to 14 kg were used. Anesthesia was induced with sodium pentobarbital (30 mg/kg, i.v.) and maintained with supplemental doses as required. A positive-pressure pump was used to ventilate the dogs through an endotracheal tube (18 strokes/minute, 20 ml/kg stroke$^{-1}$), and a heating pad kept the body temperature at 37°–38° C.

Femoral arterial blood pressure was measured through a polyethylene catheter filled with heparin solution (16 units/ml) and connected to a Statham pressure transducer. A strain-gauge arch sutured to the right ventricle of the heart measured cardiac contractility. Tension on the gauge was adjusted to 50 g and the gain of the recorder (Beckman dynograph) was set so that 50 g caused a 10-mm pen deflection. Cardiac contractile tension was measured as millimeters of pen deflection or grams of tension. The test compounds were administered as an i.v. bolus (2–5 ml) in a normal saline vehicle following a 30–45 minute equilibrium period. In a control experiment, rapid intravenous injection of 50 ml of 5 percent dextran and mechanical compression of the aorta showed that the contractility measurements were independent of changes in preload and afterload. Heart rate was derived by means of a cardiotach which was triggered by the arterial pressure pulse signal and displayed on the polygraph. The maximum effects on contractility at various dose levels were determined and plotted and the dose required to produce a 50% increase in contractility ($ED_{50}$) was determined by interpolation. The $ED_{50}$ for the compound of Example 1 was 12 mcg/kg.

The compounds of this invention may be administered by various routes including the oral, rectal, transdermal, subcutaneous, intravenous, intramuscular, or intranasal routes. It is a special feature of these compounds that they are effective positive inotropic agents, vasodilators, or bronchodilators following oral administration. The compounds are usually employed in the form of pharmaceutical compositions. Such compositions are prepared in a manner well known in the pharmaceutical art and comprise an effective amount of at least one active compound of the invention. Accordingly, the invention includes a pharmaceutical composition comprising as active ingredient a compound of Formula I associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

The compositions usually contain as active ingredient from about 1% to about 95% by weight of a compound of the invention and are preferably formulated in a unit dosage form, each dosage containing from about 0.5 to about 500 mg, more usually about 1 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The active compounds are effective over a wide dosage range and typical dosages per day will normally fall within the range of about 0.020 to about 300 mg/kg of body weight. In the treatment of adult humans, a range of from about 0.020 to about 50 mg/kg, in single or divided doses, is preferred. However, it will be understood that the amount of the compound actually administered will be determined by a physician in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following formulation examples may employ as active ingedients any of the pharmaceutical compounds of the invention. The examples are illustrative only and are not intended to limit the scope of the invention in any way.

EXAMPLE 2

Hard gelatin capsules are prepared using the following ingredients:

| | Quantity (mg/capsule) |
|---|---|
| 4,5-dihydro-6-[4-(3-pyridinyl)-phenyl]-4-ethyl-3(2H)—pyridazinone | 250 |
| Starch dried | 200 |
| Magnesium stearate | 10 |

The above ingredients are mixed and filled into hard gelatin capsules in 460 mg quantities.

EXAMPLE 3

A tablet formula is prepared using the ingredients below:

| | Quantity (mg/tablet) |
|---|---|
| 6-[4-(4-pyridinyl)-2-methyl-phenyl]-2-isopropyl-3(2H)—pyridazinone | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 4

An aerosol solution is prepared containing the following components:

| | Weight % |
|---|---|
| 6-[4-(4-methyl-2-pyridinyl)-phenyl]-4,5-dimethyl-3(2H)—pyridazinone | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remaining amount of propellant. The valve units are then fitted to the container.

EXAMPLE 5

Tablets each containing 60 mg of active ingredient are made up as follows:

| | |
|---|---|
| 4,5-dihydro-6-[3-ethyl-4-(3-pyridinyl)phenyl]-5,5-diethyl-3(2H)—pyridazinone | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 6

Capsules each containing 80 mg of medicament are made as follows:

| | |
|---|---|
| 4,5-dihydro-6-[4-(2-pyridinyl)-phenyl]-4-t-butyl-3(2H)—pyridazinone | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 7

Suppositories each containing 225 mg of active ingredient are made as follows:

| | |
|---|---|
| 6-[2-methyl-4-(4-pyridinyl)-phenyl]-2,4-dimethyl-3(2H)—pyridazinone | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 8

Suspensions each containing 50 mg of medicament per 5 ml dose are made as follows:

| | |
|---|---|
| 4,5-dihydro-6-[4-(3-pyridinyl)-phenyl]-5-ethyl-5-methyl-3(2H)—pyridazinone | 50 mg |
| Sodium carboxymethyl cellulose | 50 mg |
| Syrup | 1.25 ml |
| Benzoic acid solution | 0.10 ml |
| Flavor | q.v. |
| Color | q.v. |

| | |
|---|---|
| -continued | |
| Purified water to | 5 ml |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

I claim:

1. A compound of the formula

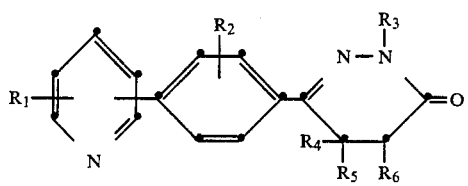

wherein $R_1$, $R_2$, $R_3$, $R_4$, $R_5$, and $R_6$ are independently hydrogen or $C_1-C_4$ alkyl, or $R_6$ and one of $R_4$ and $R_5$ taken together form a bond; and pharmaceutically acceptable acid addition salts thereof.

2. A compound according to claim 1 wherein $R_1$ is hydrogen.

3. A compound according to claim 2 wherein $R_2$ is hydrogen.

4. A compound according to claim 3 wherein $R_3$ is hydrogen.

5. A compound according to claim 4 wherein $R_6$ is hydrogen.

6. A compound according to claim 5 wherein the pyridine ring is attached at its 3-position to the phenyl substituent.

7. The compound of claim 6 which is 4,5-dihydro-6-[4-(3-pyridinyl)phenyl]-3(2H)-pyridazinone or a pharmaceutically acceptable salt thereof.

8. A method of treating a mammal, including a human subject, suffering from or susceptible to heart failure, which comprises administering to said mammal an effective amount of a compound of claim 1.

9. The method according to claim 8 employing a compound wherein $R_1$ is hydrogen.

10. The method according to claim 9 employing a compound wherein $R_2$ is hydrogen.

11. The method according to claim 10 employing a compound wherein $R_3$ is hydrogen.

12. The method according to claim 11 employing a compound wherein the pyridine ring is attached at its 3-position to the phenyl substituent.

13. The method of claim 12 employing 4,5-dihydro-6-[4-(3-pyridinyl)phenyl]-3(2H)-pyridazinone or a pharmaceutically acceptable salt thereof.

14. A pharmaceutical formulation which comprises a compound of claim 1 in association with a pharmaceutically acceptable carrier, diluent, or excipient therefor.

15. A formulation according to claim 14 employing a compound wherein $R_1$ is hydrogen.

16. A formulation according to claim 15 employing a compound wherein $R_2$ is hydrogen.

17. A formulation according to claim 16 employing a compound wherein $R_3$ is hydrogen.

18. A formulation according to claim 17 employing a compound wherein $R_6$ is hydrogen.

19. A formulation according to claim 18 employing a compound wherein the pyridine ring is attached at its 3-position to the phenyl substituent.

20. A formulation according to claim 19 employing 4,5-dihydro-6-[4-(3-pyridinyl)phenyl]-3(2H)-pyridazinone or a pharmaceutically acceptable salt thereof.

* * * * *